(12) United States Patent
Mitchell et al.

(10) Patent No.: US 8,014,490 B2
(45) Date of Patent: Sep. 6, 2011

(54) MAMMOGRAM TENDER MACHINE

(76) Inventors: Linda Mitchell, Gonzales, LA (US);
Zachary Mitchell, Gonzales, LA (US)

( * ) Notice: Subject to any disclaimer, the term of this patent is extended or adjusted under 35 U.S.C. 154(b) by 35 days.

(21) Appl. No.: 12/581,888

(22) Filed: Oct. 20, 2009

(65) Prior Publication Data
US 2011/0091010 A1    Apr. 21, 2011

(51) Int. Cl.
*A61B 6/04* (2006.01)
*H05G 1/02* (2006.01)

(52) U.S. Cl. ............ 378/37; 378/196; 378/197

(58) Field of Classification Search .......... 378/17, 378/20, 37, 196, 197, 208
See application file for complete search history.

(56) References Cited

U.S. PATENT DOCUMENTS

| | | | | |
|---|---|---|---|---|
| 5,574,763 A * | 11/1996 | Dehner | | 378/17 |
| 6,298,114 B1 * | 10/2001 | Yoda | | 378/37 |
| 6,463,122 B1 * | 10/2002 | Moore | | 378/65 |
| 6,735,274 B1 * | 5/2004 | Zahavi et al. | | 378/15 |
| 6,987,831 B2 * | 1/2006 | Ning | | 378/37 |
| 7,003,070 B1 * | 2/2006 | Chen et al. | | 378/17 |
| 7,224,764 B2 * | 5/2007 | Sukovic et al. | | 378/19 |
| 7,492,858 B2 * | 2/2009 | Partain et al. | | 378/37 |
| 7,597,104 B2 * | 10/2009 | Zheng et al. | | 128/869 |
| 7,742,796 B2 * | 6/2010 | Eberhard et al. | | 600/407 |
| 7,831,015 B2 * | 11/2010 | Li et al. | | 378/37 |
| 7,864,918 B2 * | 1/2011 | Schilling et al. | | 378/37 |
| 7,881,427 B2 * | 2/2011 | Kalender et al. | | 378/37 |

* cited by examiner

*Primary Examiner* — Allen C. Ho
(74) *Attorney, Agent, or Firm* — Michael Ries

(57) ABSTRACT

An apparatus and method of examining the breast of a woman who has difficulty in standing or raising her arms by providing an X-ray machine having x-ray emitting and receiving members that are rotatable about a vertical axis and movable up and down along the vertical axis. A cup member having an interior configured to receive one of the woman's breast is placed over a breast and suction from a source of suction is applied to the interior of the cup member to expand the breast to fill the cup. The X-ray emitting and receiving members of the X-ray machine are then oriented relative to the cup member to perform an examination of the breast inside the cup member while the woman is either in a sitting or standing position.

16 Claims, 1 Drawing Sheet

FIG. 1
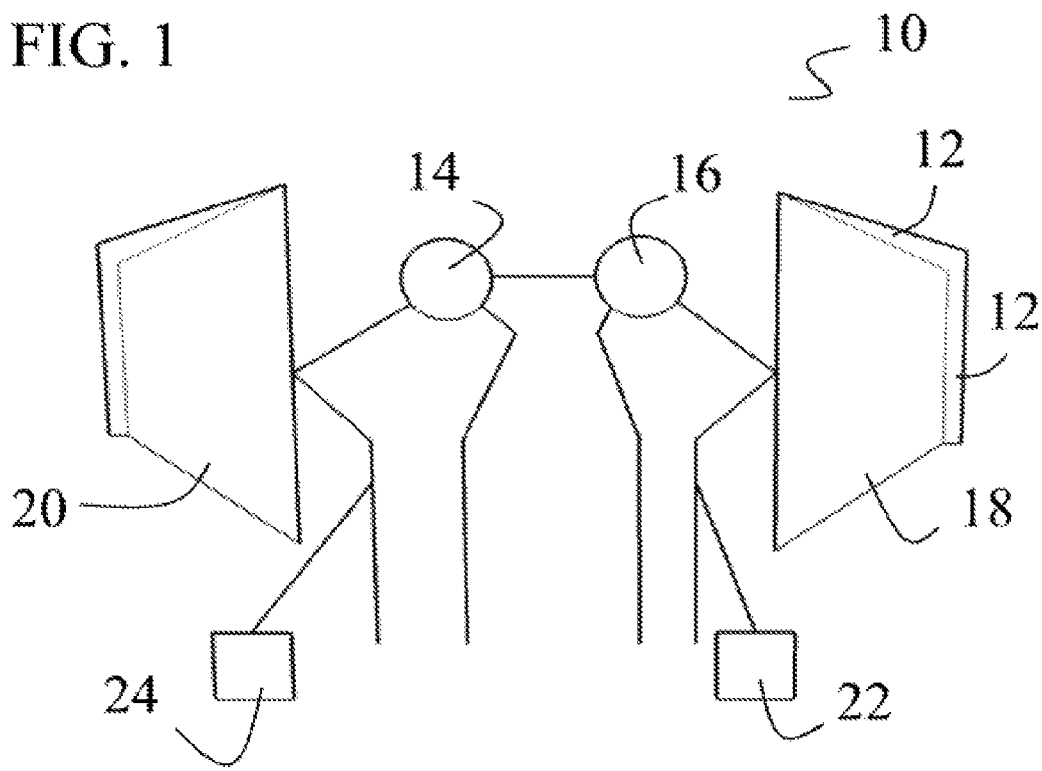
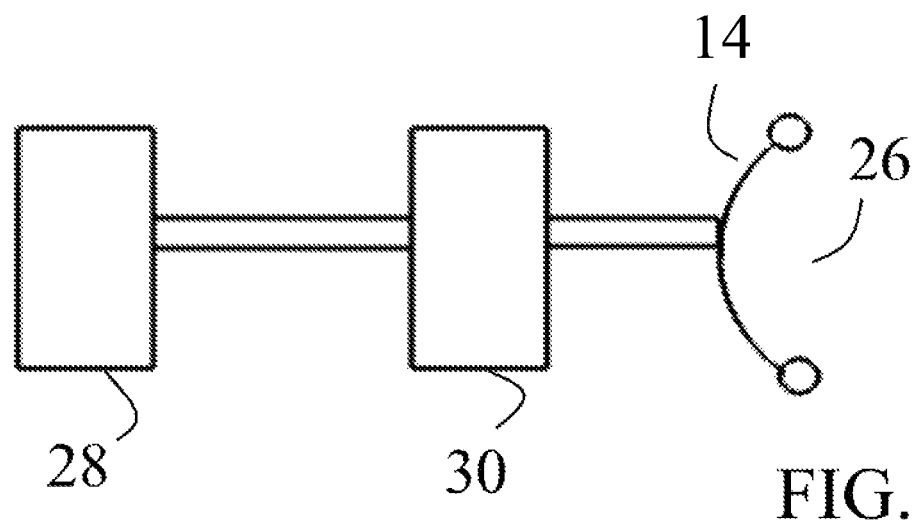
FIG. 2

MAMMOGRAM TENDER MACHINE

BACKGROUND OF THE INVENTION

1. Field of the Invention

The present invention relates to apparatus and method for positioning an X-ray imaging machine relative to a patient as opposed to positioning a patient relative to the X-ray machine in combination with a suction holding device for positioning a breast of a woman who has difficulties in raising her arms or in standing.

2. Description of Related Art

Mammography is a test that uses x-rays to generate images of the breast tissue. The test is performed to detect and evaluate abnormalities such as tumors and cysts. It is very important to perform mammograms regularly.

Successful treatment of breast cancer depends on early diagnosis. Mammography plays a major role in early detection of breast cancers. The U.S. Food and Drug Administration reports that mammography can find 85 to 90 percent of breast cancers in women over the age of 50. Clearly, the benefits of mammography far outweigh the risks and inconvenience of not having one. A screening mammogram is an x-ray examination of the breasts in a woman who has no complaints or symptoms of breast cancer. The goal of screening mammography is to detect cancer when it is still too small to be felt by a woman or her physician. Early detection of small breast cancers by screening mammography greatly improves a woman's chances for successful treatment. Screening mammography is recommended every one to two years for women once they reach 40 years of age and every year once they reach 50 years of age. Also, the current recommendation is to have a base line mammogram at the age of 35. In some instances, physicians may advise beginning screening mammography before age 40 (e.g. if the woman has a strong family history of breast cancer).

During mammography, a woman stands in front of a mammography machine and one of her breasts is placed on a clear plastic plate and gently, but firmly, pressed from another plate above her breast. This compression flattens the breast so that the maximum amount of tissue can be imaged and examined. The pressure lasts a few seconds and does not harm the breast. but can be painful The same steps are repeated with the other breast. The plates of the machine are then tilted to take a side view of each breast. When done, a woman will have two different views of each breast for a total of four pictures.

In another procedure a woman stands in front of an X-ray machine and raises her arms to elevate her breasts. With either of these procedures, a young or an older woman who has difficulty in either raising her arms or in standing will experience some degree of discomfort.

What is needed is an X-ray machine that can be positioned to screen the breast of a woman who has difficulty in either raising her arms or in standing in combination with a device that can position a woman's breast to a desired position for an X-ray examination with minimum discomfort.

SUMMARY OF THE INVENTION

In an embodiment of the present invention, there is disclosed an apparatus for examining the breast of a woman who has difficulty in standing or raising her arms by providing an X-ray machine having x-ray emitting and receiving members that are rotatable about a vertical axis and movable up and down along the vertical axis. A cup member having an interior configured to receive one of the woman's breast is placed over a breast and suction from a source of suction is applied to the interior of the cup member to expand the breast to fill the cup. The X-ray emitting and receiving members of the X-ray machine are then oriented relative to the cup member to perform an examination of the breast inside the cup member while the woman is either in a sitting or standing position.

In another embodiment there is disclosed a method of examining the breast of a woman who has difficulty in standing or raising her arms by providing an X-ray machine having x-ray emitting and receiving members that are rotatable about a vertical axis and movable up and down along the vertical axis. A cup member having an interior configured to receive one of the woman's breast is placed over a breast and suction from a source of suction is applied to the interior of the cup member to expand the breast to fill the cup. The X-ray emitting and receiving members of the X-ray machine are then oriented relative to the cup member to perform an examination of the breast inside the cup member while the woman is either in a sitting or standing position.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIG. 1 is a schematic view of an X-ray machine that can be raised or lowered and rotated about a vertical axis to accommodate a woman who has difficulties in either standing or raising her arms for a breast X-ray examination in accordance with the principles of the invention; and FIG. 2 is a side view of a breast receiving a suction holding cup in accordance with the principles of the invention.

DESCRIPTION OF THE PREFERRED EMBODIMENT

Referring to FIG. 1 there is shown a schematic view of an X-ray machine 10 that can be raised or lowered and rotated about a vertical axis using handles 12 to accommodate a woman who has difficulties in either standing or raising her arms for a breast X-ray examination. In operation, a woman either stands in position or sits in a chair, not shown, in front of the X-ray machine and two breast receiving suction cups 14, 16 are positioned over her left and right breasts. Suction is then applied to the cups to draw the breasts into the cups and properly position the breasts for an X-ray examination. The scanning 18 and receiving 20 members of the X-ray machine are movable vertically, up and down, and are rotatable about a vertical axis to position the X-ray machine relative to a part of the body that is to be examined.

The suction that is applied to the holding cups is controlled by the X-ray machine operator by foot operated control paddles 22, 24. Referring to FIG. 2, there is shown a side view of a breast receiving and suction holding cup 14, it being understood that cups 14 and 16 are similar.

Cup 14 has a hollow interior for receiving at least a portion of a woman's breast (not shown). The cup 14 can be a half of a sphere or triangular in shape, or any other convenient shape and includes an opening that is connected to a source of suction 28 through a suction regulator and gauge 30 and that maintains the level of suction at a predetermined constant level that is applied to the breast in the cup. The suction pressure that is applied to the breast is sufficient to expand the breast and to cause the skin of the breast to press against the wall of cup member 14. Thus, the breast is held steady within the cup member 14 and the suction pressure provides minimal or no discomfort to the patient while the X-ray examination procedure is being preformed. The cup member 14 is preferably made of a material which is transparent to x-rays. The interior of the cup can be lined with a soft pliable sheet of rubber or plastic which will collapse around the breast as suction is applied to accommodate breasts of different sizes. In another embodiment, various size liners can be placed inside the cup which fit the size of the breast being examined.

While there have been shown and described and pointed out the fundamental novel features of the invention as applied to the preferred embodiments, it will be understood that various omissions and substitutions and changes of the form and details of the apparatus illustrated and in the operation may be done by those skilled in the art, without departing from the spirit of the invention.

What is claimed is:

1. A structure operable for examining a breast of a woman who has difficulty in standing or raising her arms comprising:
   an X-ray machine having x-ray emitting and receiving members that are rotatable about a vertical axis and are movable up and down along the vertical axis;
   a cup member having an interior configured to receive one of the woman's breasts;
   a source of suction coupled to the interior of the cup member to expand the one of the woman's breasts to fill the cup member;
   wherein the X-ray emitting and receiving members are oriented relative to the cup member to perform an examination of the one of the woman's breasts inside the cup member while the woman is either in a sitting or standing position.

2. The structure of claim 1 wherein a level of suction applied to the interior of the cup member is controlled by an operator of the X-ray machine.

3. The structure of claim 2 wherein the cup member is composed of a material that is transparent to X-rays.

4. The structure of claim 3 wherein the interior of the cup member includes a lining that collapses around the breast as suction is applied.

5. The structure of claim 4 wherein said lining is of a flexible material.

6. The structure of claim 5 wherein said flexible lining is made of rubber.

7. The structure of claim 5 wherein said flexible lining is made of plastic.

8. The structure of claim 3 wherein the interior of the cup member is adapted to receive different breast sizes.

9. A method of examining a breast of a woman who has difficulty in standing or raising her arms comprising:
   providing an X-ray machine having x-ray emitting and receiving members that are rotatable about a vertical axis and movable up and down along the vertical axis;
   providing a cup member having an interior configured to receive one of the woman's breasts;
   applying suction from a source of suction to the interior of the cup member to expand the one of the woman's breasts to fill the cup member;
   wherein the X-ray emitting and receiving members are oriented relative to the cup member to perform an examination of the one of the woman's breasts inside the cup member while the woman is either in a sitting or standing position.

10. The method of claim 9 wherein a level of suction applied to the interior of the cup member is controlled by an operator of the X-ray machine.

11. The method of claim 10 wherein the cup member is composed of a material that is transparent to X-rays.

12. The method of claim 10 wherein the interior of the cup member includes a lining that collapses around the breast as suction is applied.

13. The method of claim 12 wherein said lining is of a flexible material.

14. The method of claim 12 wherein said flexible lining is made of rubber.

15. The method of claim 12 wherein said flexible lining is made of plastic.

16. The method of claim 10 wherein the interior of the cup member is adapted to receive different breast sizes.

* * * * *